(12) United States Patent
Pfeiffer et al.

(10) Patent No.: US 8,389,707 B2
(45) Date of Patent: Mar. 5, 2013

(54) OLIGONUCLEOTIDES RELATED TO LIPID MEMBRANE ATTACHMENTS

(75) Inventors: Indriati Pfeiffer, Göteborg (SE); Fredrick Höök, Göteborg (SE)

(73) Assignee: Bio-Rad Laboratories Inc., Hercules, CA (US)

( * ) Notice: Subject to any disclaimer, the term of this patent is extended or adjusted under 35 U.S.C. 154(b) by 1061 days.

(21) Appl. No.: 10/590,877

(22) PCT Filed: Feb. 28, 2005

(86) PCT No.: PCT/SE2005/000288
§ 371 (c)(1),
(2), (4) Date: Jul. 27, 2007

(87) PCT Pub. No.: WO2005/082922
PCT Pub. Date: Sep. 9, 2005

(65) Prior Publication Data
US 2007/0275047 A1    Nov. 29, 2007

Related U.S. Application Data

(60) Provisional application No. 60/548,149, filed on Feb. 26, 2004.

(51) Int. Cl.
C07H 21/04    (2006.01)
C07H 21/02    (2006.01)
C12Q 1/68    (2006.01)
(52) U.S. Cl. .................. 536/24.2; 536/23.1; 435/6.1
(58) Field of Classification Search .................. None
See application file for complete search history.

(56) References Cited

U.S. PATENT DOCUMENTS 7,615,539 B2 * 11/2009 Uhlmann et al. ........... 514/44 R

FOREIGN PATENT DOCUMENTS

WO    0233045    4/2002

OTHER PUBLICATIONS

Mammen et al, "Polyvalent Interactions in Biological Systems: Implications for Design and Use of Multivalent Ligands and Inhibitors," Agnew. Chem. Int. Ed. vol. 37, pp. 2754-2794 (1998).
Bijsterbosch, Martin K. et al, "bis-Cholesteryl-Conjugated Phosphorothioate Oligodeoxyucleotides Are Highly Selectively taken Up by the Liver", *The Journal of Pharmacology and Experimental Therapeutics*, 2002, vol. 302, No. 2, pp. 619-626.
Fang, Ye et al, "Membrane Protein Microarrays", *J. Am. Chem. Soc.*, 2002, vol. 124, No. 11, pp. 2394-2395.
Svedhem, Sofia et al, "Pattersn of DNA-Labeled and scFv-Antibody-Carrying Lipid Vesicles Directed by Material-Specific Immobilization of DNA and Supported Lipid Bilayer Formation on an Au/Si02 Template", *ChemBioChem*, 2003, No. 4, pp. 339-343.
Pfeifer, Indriati et al, "Bivalent Cholesterol-based Coupling of Oligonucletides to Lipid Membrane Assemblies", *J. Am. Chem. Soc.*, 2004, vol. 126, pp. 10224-10225.
Zhang, et al, "Informational Liposomes: Complexes Derived from Cholesteryl-conjugated Oligonucleotides and Liposomes," Tetrahedron Letters, vol. 37, No. 35, pp. 6243-6246 (1996).

* cited by examiner

*Primary Examiner* — Doug Schultz
(74) *Attorney, Agent, or Firm* — Porter Wright Morris & Arthur LLP

(57) ABSTRACT

Oligonucleotide structures are provided that are capable of forming more stable bonds to a lipid membrane and thereby generate an improved control of the process whereby oligonucleotide linkers are introduced to lipid membranes. Methods of forming lipid membrane oligonucleotide attachments are provided including lipid vesicles. The oligonucleotides typically comprise at least two hydrophobic anchoring moieties capable of being attached to a lipid membrane. Said moieties may be attached at the terminal ends of an oligonucleotide or, in the case of a first and second strand forming a duplex, at the same terminal end one of the strands other end not being part of the duplex leaving it free to hybridize to additional strands. The lipid vesicles attached with the oligonucleotide can be used in biosensors and may contain membrane proteins.

19 Claims, 3 Drawing Sheets

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide

<400> SEQUENCE: 1
tagttgtgac gtacacccc                                        20

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide

<400> SEQUENCE: 2
tatttctgat gtccacccc                                        20

<210> SEQ ID NO 3

-continued

<211> LENGTH: 20
<212> TYPE: DNA
<213> ORGANISM: Artificial Sequence
<220> FEATURE:
<223> OTHER INFORMATION: Oligonucleotide

<400> SEQUENCE: 3
tgtacgtcac aactaccccc                                        20

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide

<400> SEQUENCE: 4
tggacatcag aaataccccc                                        20

<210> SEQ ID NO 5
<211> LENGTH: 30
<212> TYPE: DNA
<213> ORGANISM: Artificial Sequence
<220> FEATURE:
<223> OTHER INFORMATION: Oligonucleotide

<400> SEQUENCE: 5
tagttgtgac gtacaaagca ggagatcccc                             30

<210> SEQ ID NO 6
<211> LENGTH: 30
<212> TYPE: DNA
<213> ORGANISM: Artificial Sequence
<220> FEATURE:
<223> OTHER INFORMATION: Oligonucleotide

<400> SEQUENCE: 6
tatttctgat gtccaagcca cgagatcccc                             30

<210> SEQ ID NO 7
<211> LENGTH: 15
<212> TYPE: DNA
<213> ORGANISM: Artificial Sequence
<220> FEATURE:
<223> OTHER INFORMATION: Oligonucleotide

<400> SEQUENCE: 7
cccgatctcc tgctt                                             15

<210> SEQ ID NO 8
<211> LENGTH: 15
<212> TYPE: DNA
<213> ORGANISM: Artificial Sequence
<220> FEATURE:
<223> OTHER INFORMATION: Oligonucleotide

<400> SEQUENCE: 8
cccgaactcg tggct                                             15

OLIGONUCLEOTIDES RELATED TO LIPID MEMBRANE ATTACHMENTS

RELATED APPLICATIONS

This application is a 371 of PCT/SE2005/000288 filed Feb. 28, 2005 and claims priority under 35 U.S.C. §119 of U.S. Application Ser. No. 60/548,149 filed Feb. 26, 2004.

BACKGROUND OF THE INVENTION

Rapid progress in protein-chip technologies is today made with respect to water soluble proteins (Kodadek, T., *Chemistry and Biology* 2001, 8, 105-115), but to generate a signature of the whole proteome make-up also membrane proteins, which constitute an important group of proteins being a common target for disease diagnostics and therapeutic drugs, must also be addressable. However, this class of proteins are often identified as an extremely difficult group of proteins to be analysed on this format. In fact, the first low-density protein chip based on membrane proteins was only recently reported (Fang, Y.; Frutos, A. G.; Lahiri, J., *Journal of the American Chemical Society* 2002, 124, (11), 2394-2395), demonstrating an array produced via micro-dispensing of G protein-coupled receptor (GPCR) containing lipid membranes. To fully explore the potential of array-based analysis of membrane proteins, tethered lipid vesicles have recently emerged as a most promising alternative, non-the least since they offer the possibility to measure also membrane-protein mediated material transport across the membrane (Stamou, D.; Duschl, C.; Delamarche, E.; Vogel, H., *Angewandte Chemie-International Edition* 2003, 42, (45), 5580-5583). Means to control the positioning of different types of vesicles on pre-defined regions are still, to a large extent, lacking. By combining the concept of DNA-labeled vesicles (Patolsky, F.; Lichtenstein, A.; Willner, I., *Journal of the American Chemical Society* 2000, 122, (2), 418-4) previously utilized for signal enhancement of DNA hybridization detection (with the concept of using DNA-labeled biomolecules for site-selective binding on cDNA arrays (Niemeyer, C. M., *Science* 2002, 297, (5578), 62). It has recently been demonstrated by the present inventors (Svedhem, S.; Pfeiffer, I.; Larsson, C.; Wingren, C.; Borrebaeck, C.; Höök, F., *Chem Bio Chem* 2003, (4), 339-343) and others (Yoshina-Ishii, C.; Boxer, S. G., *Journal of the American Chemical Society* 2003, 125, (13), 3696-3697) to use low density cDNA arrays for site-selective and sequence specific coupling of DNA-tagged lipid vesicles. Instead of using covalent coupling of DNA to chemically active lipids (Yoshina-Ishii, C et al and the article Patolsky, F.; Katz, E.; Bardea, A.; Willner, I., *Langmuir* 1999, 15, (11), 3703-3706), we made use of cholesterol-modified ss-DNA for spontaneous anchoring into the hydrophobic interior of lipid membranes. This means of anchoring DNA adds a three-folded advantage. This is so because the method (i) is faster (tens of minutes compared with hours), (ii) does not require chemically modified lipids to be introduced and (iii) makes use of a naturally occurring membrane constituent, thus eliminating the risk for side effects induced by chemically reactive lipid head groups on incorporated membrane constituents. However, the cholesterol-based anchoring of DNA to lipid membranes turns out to be relatively weak, thus complicating quantitative control of the number of DNA per vesicles. In addition, site selective sorting of differently DNA-tagged vesicles to cDNA arrays, must, due to DNA exchange between differently tagged vesicles, be accomplished in a sequential, rather than parallel manner (see above recited articles by Svedhem et al Yshina-Ishii et al)

SUMMARY OF INVENTION

The present invention aims to provide oligonucleotide structures that are capable of forming more stable bonds to a lipid membrane and thereby generate an improved control of the process whereby oligonucleotide linkers are introduced to lipid membranes. The invention is also directed at methods of forming lipid membrane oligonucleotide attachments and lipid vesicles provided with such oligonucleotides, as well as methods of forming such vesicles.

DESCRIPTION OF INVENTION

To facilitate an understanding of the present invention, a number of terms are defined below.

As used herein, the term "vesicle" or "liposome" refers typically to spherical structures (5 nm to 20 µm in diameter) built up by lipid membranes, which may or may not contain proteins, glycolipids, steroids or other membrane-associated components. The terms "liposome" and "vesicle" are used interchangeable herein. Vesicles can be naturally (eg the vesicles present in the cytoplasm of cells that transport molecules and partition specific cellular functions) or synthetically (eg liposomes) generated. The term "vesicle" is here also used for "micelles" which are particles comprising of lipids, which particles have a hydrophilic exterior and a hydrophobic interior.

As used herein, the term "nucleotide" refers to any nucleic acid, such as DNA and RNA, as well nucleic acid analogues such as, but not limited to, PNA (Peptide Nucleic Acid), LNA (Locked Nucleic Acid) and Morpholino nucleic acid analogues. The term also relates to any nucleotide comprising of the known base analogues of DNA and RNA.

As used herein the term "oligonucleotide" refers to a short length of p single-stranded polynucleotide chain. Oligonucleotides are typically less than 100 residues long, however, as used herein, the term is also intended to encompass longer polynucleotides. The term refers to all combinations of nucleotides as defined above, forming a polymer of nucleotides.

As used herein, the term "hybridisation" is used in reference to the pairing of essentially complementary nucleic acids often referred to as Watson-Crick-hybridisation as well as the hybridisation referred to as Hoogsteen-hybridisation. As used herein, the term "immobilisation" refers to the attachment or entrapment, either chemically or otherwise, of material to a transducer surface in a manner that confines, but not necessarily restricts, the movement of the material.

As used herein, the term "analytes" refers to any material that is to be analysed.

As used herein, the term "biosensors" refers to any sensor device that is partially or entirely composed of biological molecules. In a traditional sense, the term refers to "an analytical tool or system consisting of an immobilised biological material (such as enzyme, antibody, whole cell, organell, or a combination thereof) in intimate contact with a suitable transducer device which will convert the biochemical signal into a quantifiable electrical signal" (Gronow, Trends Biochem Sci 9, 336, 1984).

As used herein, the term "multilayer" refers to structures comprised of at least a second layer formed on top of a first layer. The individual layers may or may not interact with one another.

As used herein, the term "biologically active compound" refers to biological compounds that are capable of interacting with other material or compounds. Such biologically active compounds can include, but are not limited to, proteins, antibodies, nucleotides, lipids, carbohydrates and combinations thereof. The terms "receptor" and "biologically active compound" are used interchangeable herein.

As used herein, the term "membrane protein" refers to proteins or polypeptides, which are connected to or inserted in a lipid membrane in a lipid layer.

As used herein, the term outwardly projecting compound" refers to a compound with a part that is projecting out from a surface. In the case where the surface is essentially spherical, as in the case with vesicles, the term means that the compounds project from the surface towards the surroundings.

As used herein, the term "surface" shall be used in its widest sense. It encompasses all compound that can be used a support means on which structures can be immobilized.

As used herein, the term "linker adapted for binding" refers to that the linker comprises a compound with ability to bind to another compound.

As used herein, the term "linker available for binding" refers to that a linker is adapted for binding, but the linker is not yet bound to another linker, or that all binding sites of the linker are not yet occupied.

In its most general terms the present invention refers to an oligonucleotide comprising at least two hydrophobic anchoring moieties capable of being attached to a lipid membrane. The anchoring moieties serve to bind directly to the lipid membrane by hydrophobic interaction at adjacent sites of the membrane and aim essentially to permanently attach the oligonucleotide which may in turn be provided with multiple biological functions according established techniques and serve may as a linker to build up multilayered surfaces of the type as explained in our parallel application SE 03 01038-6 and further below.

Also in general terms, the present invention refers to a method of forming a lipid membrane attached linker, wherein an oligonucleotide having two or more hydrophobic anchoring moieties contact a lipid membrane, thereby accomplishing a direct attachment of said oligonucleotide by said moieties at adjacent sites on the same membrane. Preferably, the membrane forms a lipid vesicle and the membrane is a bilayer membrane. The method enables a surprisingly strong coupling of the oligonucleotide to the membrane that is practically irreversible.

Preferably, the hydrophobic anchoring moieties are located in the oligonucleotide terminal ends and the lipid membrane is the part of lipid vesicle. In one aspect, the oligonucleotide comprises a first strand and a second strand of nucleic acid, said two strands being hybridised to each other in a duplex section in a manner that the first strand terminal end is not a part of said duplex section and is free from a hydrophobic anchoring moiety. Preferably, the hydrophobic anchoring moieties are covalently attached to the adjacent terminal ends of said first and second strands.

In another aspect polyvalent oligonucleotides can be assembled so as to provide multiple (more than two) attachment points to the lipid membrane. The present inventors contemplate that the need to increase the number of hydrophobic anchoring units may occur as a result of using longer nucleic acids with higher water solubility. For this purpose, the present invention is alternatively directed at oligonucleotides comprising n additional strands to the first and second strand (n being an integer and n>0). Each additional strand is provided with a terminal hydrophobic anchoring moiety, wherein a first additional strand is hybridized to said second strand and wherein a second additional strand is hybridized to the first additional strand and strand n is hybridized to strand n-1.

In still another aspect, the oligonucleotides can be construed to constitute links to create multiplayer structures including a plurality of lipid vesicles, or other assemblies useful when designing chemically or biologically active surfaces. Such oligonucleotides comprises a first and a second strand said two strands being hybridized to each other in a duplex region in a manner that leaves the first strand free to hybridize with a third strand. The free end of the first strand may also include other agents, such as labelling agent, an antibody, a capturing agent capable of extracting desirable agents from a surrounding fluid or a conventional agent with specific binding capacity. In one embodiment of this aspect, the oligonucleotide will have a first strand with hydrophobic anchoring moieties in both its terminal ends to which strand a third strand with, or without, a terminal hydrophobic anchoring moiety can be hybridized, so first and third strands have adjacent hydrophobic anchoring moieties.

The hydrophobic anchoring moiety is selected among, for example, steroids, fatty acids, hydrophobic peptides and lipids; most preferably the hydrophobic anchoring moiety is cholesterol or a derivative thereof.

In order to form a suitably flexible structure with an optimum possibility to associate with the hydrophobic parts of the lipid membrane, the inventive oligonucleotides have the hydrophobic anchoring moieties spaced apart from the duplex section by a spacing group or a sufficient number of non-hybridized nucleic acid units. In order to obtain oligonucleotide structures with optimal flexibility/rigidity by the chain length between the duplex section and the chain chemistry can be modified.

The oligonucleotide can be generally adapted and available to be linked by specific binding to a surface immobilized linker or to another lipid membrane attached linker. The linkage can be mediated with nucleic acid hybridisation or by other types of specific binding well understood to skilled persons. For example, the oligonucleotides can comprising a section of peptide nucleic acids (PNA) capable of forming PNA-peptide complexes. Alternatively, the oligonucleotides can be immobilized directly to surface, either to a lipid membrane or to another suitable compound or structure, for example by the free end of the first strand. There are numerous routes to enable surface immobilization of nucleic acids known and available to artisans in this field and no further discussion is necessary in the present context.

According to a preferred embodiment of the present invention, the first strand is longer (i.e. includes more nucleic acid units) than the second strand. The first and second strands preferably have a duplex region involving the terminal end of the second strand. According to one suitable example, the first strand has essentially double the amount of nucleic acid monomers than the second strand, said first and second strand have a cholesterol molecule attached to their free 5' and 3'-ends, respectively. According to a specific example, the oligonucleotides have a first strand of a 30mer DNA and the second strand of a 15-mer DNA having 12 complementary bases.

The oligonucleotides are preferably to be attached to lipid vesicles. The so formed lipid vesicles can be designed with different additional functionalities. For example such lipid vesicles can contain electrochemically detectable reporter molecules in a manner outlined by WO 02/081739 and WO 02/081738 which both are incorporated as references. The lipid vesicles may include biologically active compounds exhibiting biological functionality, such as membrane proteins, as discussed in more detail in the aforementioned SE 0301038-6.

The present invention is further directed at surface immobilized structures comprising a plurality of vesicles having membrane attached oligonucleotides of the above mentioned features. To build up such structures, the vesicles are adapted and available to be linked by specific binding to any of a surface immobilized linker, another lipid vesicle attached linker or to the type of surface immobilized oligonucleotide mentioned above. The surface immobilized structures can typically be used in biosensors, but numerous other applications would also be conceivable.

DETAILED AND EXEMPLIFYING PART OF THE DESCRIPTION

Figures 1A, 1B:
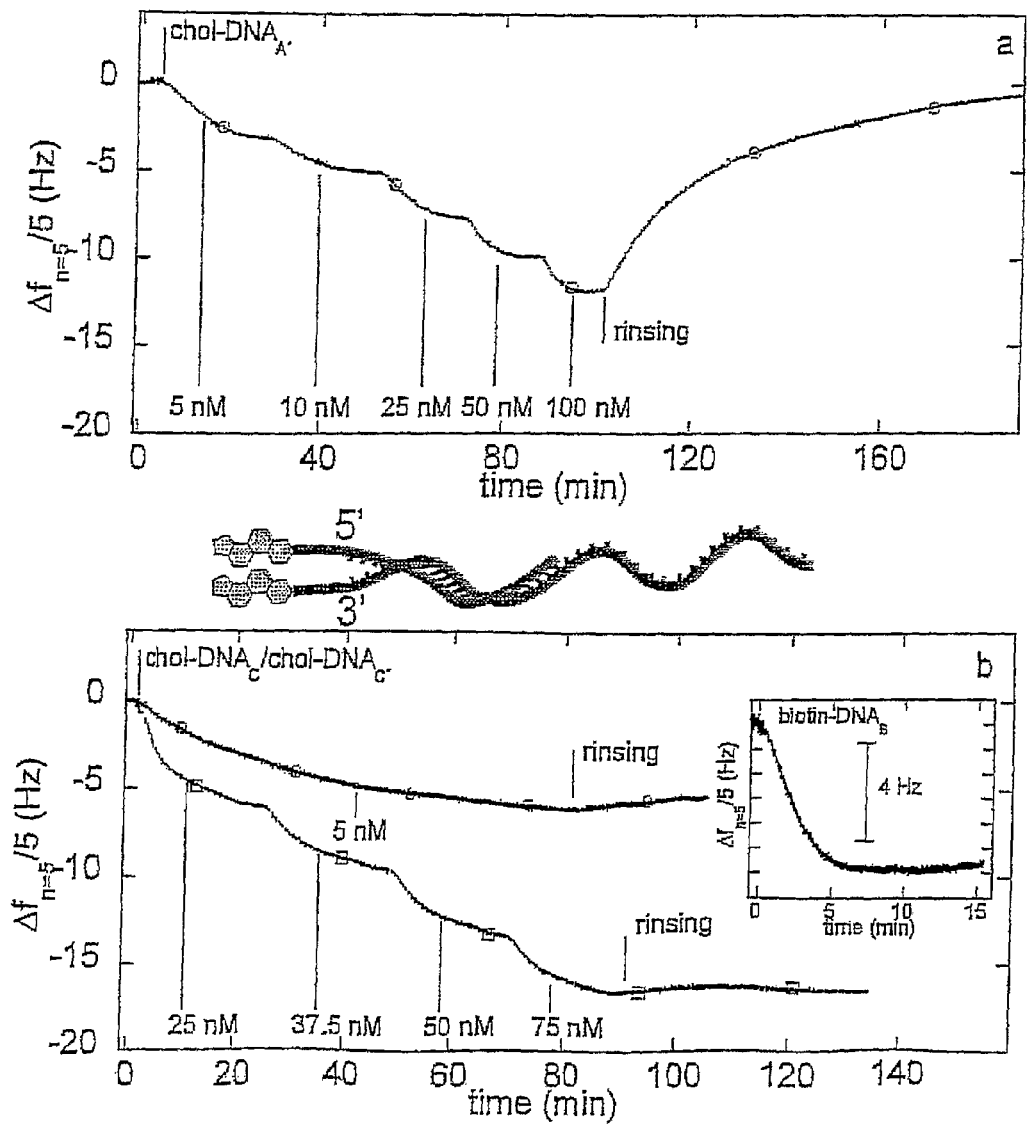
FIG. 1 shows a bivalent cholesterol based oligonucleotide and changes in coupled mass from quartz microbalance with dissipation monitoring measurements upon stepwise addition different cholesterol-DNA assemblies.

By mimicking Natures way of utilizing multivalent interactions we present in the present work a novel means of improving the strength of cholesterol-based DNA coupling to lipid membranes (Mammen, M.; Choi, S. K; Whitesides, G. M., *Angewandte Chemie-International Edition* 1998, 37, (20), 2755-2794). A bivalent cholesterol-based coupling of DNA was accomplished by hybridization between a 15-mer DNA and a 30-mer DNA, being modified with cholesterol in the 3'- and 5'-end, of respectively (FIG. 1).

Water was deionized and filtered (MilliQ unit, Millipore). DNA strands:5'-TAG TTG-TGA-CGT-ACA-CCC-CC-3' (SEQ ID NO 1, $DNA_{A'}$); 5'-TAT-TTC-TGA-TGT-CCA-CCC-CC-3' (SEQ ID NO 2, $DNA_{B'}$); 5'-TGT-ACG-TCA-CAA-CTA-CCC-CC-3' (SEQ ID NO 3, $DNA_A$); 5'-TGG-ACA-TCA-GAA-ATA-CCC-CC-3' (SEQ ID NO 4, $DNA_B$); 5'-TAG-TTG-TGA-CGT-ACA-AAG-CAG-GAG-ATC-CCC-3' ( SEQ ID NO 5, $DNA_C$); 5'-TAT-TTC-TGA-TGT-CCA-AGC-CAC-GAG-ATC-CCC-3' (SEQ ID NO 6, $DNA_D$); 5'-CCC-GAT-CTC-CTG-CTT-3' (SEQ ID NO 7, $DNA_{C'}$), 5'-CCC-GAA-CTC-GTG-GCT-3' (SEQ ID NO 8, $DNA_{D'}$), derivatised at the 3'-end with biotin (biotin-$DNA_B$) or cholesterol (chol-$DNA_{A'}$; chol-$DNA_B$; chol-$DNA_{B'}$) or at the 5'-end with cholesterol (chol-$DNA_C$, chol-$DNA_{C'}$, chol-$DNA_D$, chol-$DNA_{D'}$) (MedProbe, Norway). Stock solutions of DNA conjugates (20 µM in Buffer I: 10 mM Tris, 1 mM EDTA, pH 8.0) and proteins (biotin-labeled BSA (Sigma, 1 mg/mL in water), neutravidin (Pierce, 1 mg/mL in Buffer II: 10 mM Tris, pH 8.0, 100 mM NaCl) were aliquoted and stored at −20° C. 1-Palmitoyl-2-Oleoyl-sn-Glycero-3-Phosphocholine (POPC, Avanti Polar Lipids, Ala., USA) was dissolved in chloroform. For fluorescent vesicles, 0.5% (w/w) of Lissamine™ rhodamine B 1,2-dihexadecanoyl-sn-glycero-3-phosphoethanolamine (rhodamine-DHPE) (Molecular Probes, USA) or 2-(12-(7-nitrobenz-2-oxa-1,3-diazol-4-yl) amino)dodecanoyl-1-hexadecanoyl-sn-glycero-3-phosphocholine (NBD-HPC) (Molecular Probes, USA) was added to the lipid solution. Lipid vesicles were prepared by evaporation of the solvent under $N_2$ (>1 h), followed by hydration in buffer (5 mg/mL) and extrusion through 0.1 and 0.03 µm polycarbonate membranes 11× each (Whatman, USA), stored at 4° C. under $N_2$ DNA-labeling was achieved by addition of 0.5% (w/w) of chol-DNA to the vesicle solution, corresponding to ~4 DNA per vesicle. All experiments were made be dissolving the stock solutions in Buffer II to given concentrations. Substrates (AT-cut quartz crystals, $f_0$=5 MHz, with either gold or $SiO_2$) and the QCM-D instrument (Q-sense D 300) were from Q-sense AB, Sweden. The crystals were cleaned in 10 mM SDS (>15'), followed by 2× rinsing with water, drying ($N_2$), and UV-ozone treatment (10'). The microscope used for imaging was a Zeiss Axioplan 2 fluorescence microscope. $SiO_2$-coated crystals were patterned by evaporation of 3 nm of Ti and 100 nm of Au through a mask.

The detailed design of the construct was defined by choosing 12 bases on the 30-mer strand to be complementary to 12 bases on 15-mer strand. The sequences were chosen such that the duplex formed by incubating these strands forced the two cholesterol moieties into close proximity, still separated from the duplex region by a pair of non-hybridized (3C) spacers.

FIG. 1a shows changes in f (c.f. coupled mass) from quartz crystal microbalance with dissipation monitoring (QCM-D) measurements upon stepwise addition of chol-$DNA_{A'}$ at increasing concentrations to a SPB-coated $SiO_2$ surface, formed as described previously (CA Keller et al. Biophysical Journ. 75(3), 1397-1402). Temporal variations in f obtained upon addition of (blue) chol-$DNA_C$ after spontaneous formation of an SPB (t=2 to 4 min) on a $SiO_2$-coated QCM sensor surface at increasing concentrations: 5, 10, 25, 50, 100 nM at a flow rate of 250 µL/min. After saturated binding at 100 nM, the system was thoroughly rinsed in buffer, demonstrating fully reversible binding in agreement with a Langmuir-adsorption behavior (due to the fact that water entrapped in the DNA film is sensed by QCM, see e.g. 14, changes in f cannot be used to quantify the amount of coupled mass, but were used for a relative comparison of coupled mass vs. concentration only) revealing $K_d(=k_{off}/k_{on})$ and $k_{off}$ values of 16.7±4 nM and ~5.8×10$^{-4}$ s$^{-1}$, respectively (addition of the 30-mer chol-$DNA_C$ displays kinetics similar to that of chol-$DNA_{A'}$ and chol-$DNA_{B'}$ (not shown)).

With reference to FIG. 1b, the same type of data as in the experimental context demonstrated with FIG. 1a, obtained upon addition of the DNA construct comprised of pre-hybridized (30 min incubation) chol-$DNA_C$ and chol-$DNA_{C'}$ upon increasing concentration: 25, 37.5, 50 and 75 nM and 5 nM, only. After saturated binding, the solutions were exchanged to pure Buffer II. Also shown as an inset is an addition of biotin-$DNA_B$, being complementary to 15 free hanging bases on the chol $DNA_C$/chol-$DNA_{C'}$ duplex construct. The binding of the duplex construct (chol-$DNA_C$/chol-$DNA_{C'}$) carrying two cholesterol moieties displays irreversible coupling (see FIG. 1b) independent on concentration. This excludes a Langmuir-based analysis of the data, but shows that $k_{off}$ is reduced by at least one order of magnitude compared with the monovalent coupling. Thus, under the assumption that $k_{on}$ is similar for the mono- and bivalent coupling (see the above recited article by M Mammen et al.) the affinity constant (1/$K_d$) is, at least, one order of magnitude higher for the bivalent coupling. Even if the increase in the binding strength may very well be larger than so, and even approach the theoretical value of (1/$K_d$)$^2$, the most important observation is that the coupling is irreversible.

First, this means that the bivalent coupling can be used to precisely control the number of DNA per lipid-membrane area. Second, the rapid binding upon addition of fully complementary biotin-$DNA_B$ (inset in FIG. 2b), demonstrates the feasibility of this template for detailed DNA-hybridization kinetics studies. Third, exchange of DNA between differently DNA-modified vesicles is likely to be significantly reduced.

Figure 2:
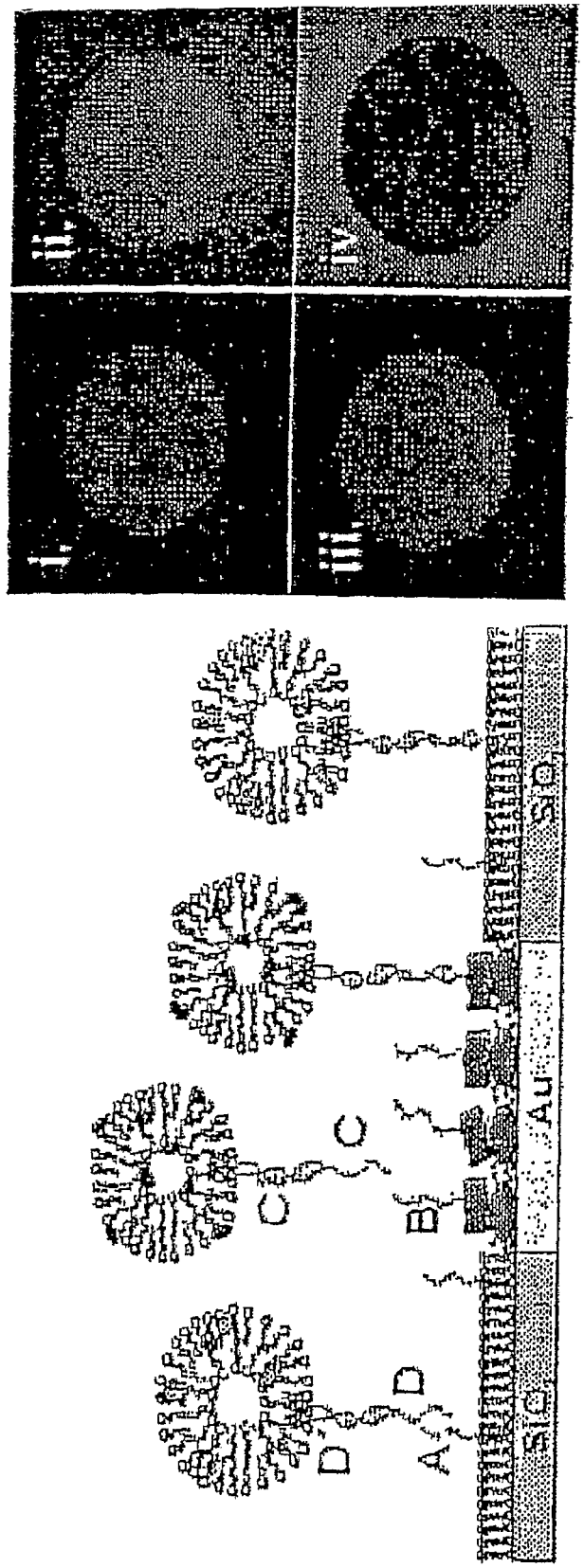
FIG. 2 shows a schematic illustration of the DNA array produced a described in the specification and micrographs illustrating the sorting of differently DNA-tagged vesicles.
Figure 3:
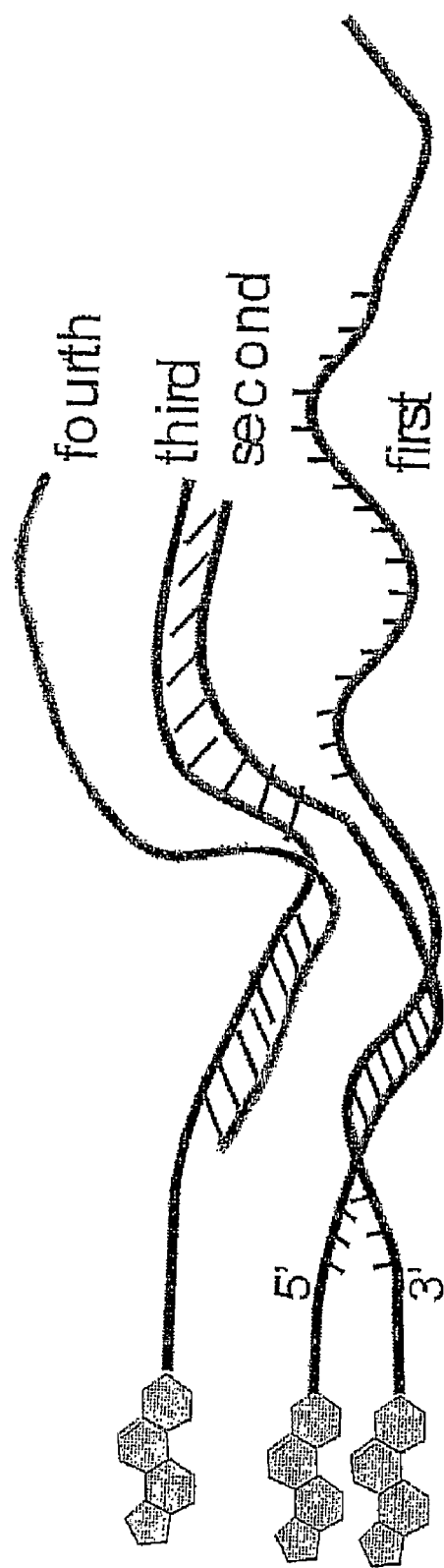
FIG. 3 shows a schematic example of a polyvalent oligonucleotide with more than two hydrophobic anchoring moieties available lipid membrane attachment.

To test the latter hypothesis, the bivalent cholesterol coupling was tested by producing biotin-DNA$_B$-modified gold spots surrounded by a planar SPB modified with chol-DNA$_A$, thus comprising the simplest possible "cDNA array" (FIG. 2).

Referring to FIG. 2 (Left) showing a schematic illustration of the DNA array produced as described previously (see the above article by Svedhem et al) In brief, the surface pattern was modified by preferential adsorption of biotin-BSA (10 μγ/μL) to the Au spots over the surrounding $SiO_2$, followed by addition of POPC lipid vesicle solution (20 microgram/mL), rendering the surrounding $SiO_2$ substrate modified with an SPB whereas only weak adsorption occur to the biotin-BSA modified gold spots (Svedhem et al.). This was then followed by subsequent additions of (i) neutravidin (10.0 microgram/mL), biotin-DNA$_B$ (0.1 microM) and chol-DNA$_A$ (0.1 microM). FIG. 2 (Right) shows micrographs (i-iv) illustrating the sorting of differently DNA-tagged vesicles obtained by exposing the DNA-modified substrate to a mixture of Rhodamine-labeled vesicles (exc.=550 nm/em.=590 nm) and NBD-labeled vesicles (exc.=460 nm/em.=550 nm) being modified with: chol-DNA$_{A'}$ and chol-DNA$_{B'}$, respectively (micrographs i and ii), and bivalently-coupled DNA constructs comprised of chol-DNA$_C$/chol-DNA$_{C'}$ and chol-DNA$_D$/chol-DNA$_{D'}$, respectively. The DNA concentration was adjusted to ~4 DNA per vesicle. The vesicle suspensions were incubated for five minutes prior to exposure, and analyzed after 30 min with a green filter (exc.=450-490 nm/em.=515-565 nm) for image ii) and iv) and a red filter (exc.=546 nm/em.=590 nm) for image i) and ii).

To evaluate parallel sorting from a mixture of two types of vesicles, the "cDNA array" was exposed to two types of vesicle suspensions. One contained two differently fluorescent labeled vesicles (red and green) being modified with chol-DNA$_{A'}$ and chol-DNA$_{B'}$, respectively, (c.f. FIG. 1a). The other contained the same types of vesicles being separately modified via bivalently coupled DNA constructs, carrying single stranded regions complementary to the immobilize chol-DNA$_A$ and biotin-DNA$_B$, respectively (c.f. inset in FIG. 1b). Indeed, the vesicle suspension containing vesicles tagged with the bivalently coupled DNA demonstrates sequence specific and site selective binding to the predefined regions on the surface (iii. and iv in FIG. 2), whereas the monovalently modified vesicles appears to be distributed on both regions (i. and ii. in FIG. 2). The over all lower fluorescence on the SPB substrate is attributed to the lower coverage of chol-DNA$_B$ than biotin-DNA$_A$, and the weak fluorescent dots on the spot in image iv.) is attributed to chol-DNA$_A$ binding to non-specifically adsorbed lipid vesicles to biotin-BSA during the SPB formation process (see Figure Legend).

Even if the strength of the bivalent cholesterol-based coupling must not necessarily by higher than that obtained upon covalent coupling to an activated lipid head group, we emphasize the simplicity of the principle and its broad application areas, including a large variety of lipid assemblies, such as, for example, lipid vesicles produced by cells or formed from crude cell membranes (to be published). Furthermore, the successful use of a DNA-modified SPB for hybridization detection under controlled flow conditions (FIG. 1b), points towards an interesting template for drug-, protein- and DNA-DNA interaction studies. This is in particular so, since the DNA coverage can be precisely controlled, which is known to be critical in the case of immobilized DNA (Larsson, C.; Rodahl, M.; Hook, F., *Analytical Chemistry* 2003, 75, (19), 5080-5087 and Shchepinov, M. S.; CaseGreen, S. C.; Southern, E. M., *Nucleic Acids Research* 1997, 25, (6), 1155-1161). Furthermore, the commonly used streptavidin templates used for these purposes may in certain cases induce unwanted non-specific protein binding, which is likely to be significantly reduced in this case. Finally, our means of utilizing DNA as a building block to construct a bivalent coupling is easily extended to DNA constructs rendering multivalent interactions, thus comprising a simple model system for fundamental studies to support, for example, recent theoretical development in this field (Kitov, P. I.; Bundle, D. R., *Journal of the American Chemical Society* 2003, 125, (52), 16271-16284).

The invention claimed is:

1. An oligonucleotide structure, comprising
a first strand of nucleic acid and a second strand of nucleic acid, the first and second strands being hybridized to each other in a duplex section, and
at least two hydrophobic anchoring moieties capable of being attached to a lipid membrane,
wherein a terminal end of the first strand is not part of the duplex section and is free from a hydrophobic moiety,
wherein the hydrophobic anchoring moieties are covalently attached to adjacent terminal ends of the first and second strands, respectively, and
wherein the oligonucleotide structure is immobilized to a surface by binding to a surface-immobilized linker or by binding to a lipid membrane-attached linker.

2. An oligonucleotide structure according to claim 1, comprising at least one additional strand, wherein each additional strand is provided with a terminal hydrophobic anchoring moiety, wherein a first additional strand is hybridized to said second strand and wherein any second or greater additional strand is hybridized to the preceding additional strand.

3. An oligonucleotide structure according to claim 1, wherein the two strands are hybridized to each other in the duplex region in a manner that leaves the first strand free to hybridize with a third strand.

4. An oligonucleotide structure according to claim 3, wherein said second strand has hydrophobic anchoring moieties in both terminal ends.

5. An oligonucleotide structure according to claim 1, wherein the hydrophobic anchoring moieties are selected among steroids, fatty acids, hydrophobic peptides and lipids.

6. An oligonucleotide structure according to claim 5, wherein the hydrophobic anchoring moieties are cholesterol or a derivative thereof.

7. An oligonucleotide structure according to claim 1, wherein each hydrophobic anchoring moiety is spaced apart from the duplex section by a spacing group or a sufficient number of non-hybridized nucleic acid units.

8. An oligonucleotide structure according to claim 1, wherein the first strand is longer than the second strand, and said first and second strands have a duplex region involving the terminal end of the second strand.

9. An oligonucleotide structure according to claim 1 comprising a section of peptide nucleic acids (PNA) capable of forming PNA-peptide complexes.

10. An oligonucleotide structure according to claim 5, wherein the first strand is 30-mer DNA; and the second strand is a 15-mer DNA having 12 complementary bases.

11. A lipid vesicle comprising an oligonucleotide structure according to claim 1 attached to its lipid membrane.

12. A lipid vesicle according to claim 11 comprising electrochemically detectable reporter molecules.

13. A lipid vesicle according to claim 11 comprising biologically active compounds exhibiting biological functionality.

14. A lipid vesicle according to claim 13, wherein said biologically active compound is a membrane protein.

15. A biosensor including a surface immobilized oligonucleotide structure according to claim 1.

16. A method of forming a lipid membrane attached linker, comprising contacting an oligonucleotide structure according to claim 1 having two or more hydrophobic anchoring moieties with a lipid membrane, thereby accomplishing a direct attachment of said oligonucleotide structure by said moieties at adjacent sites on the same membrane.

17. A method according to claim 16, wherein said membrane forms a lipid vesicle.

18. A method according to claim 16 wherein said membrane is a bilayer membrane.

19. A method according to claim 16, wherein said attachment is irreversible.

* * * * *